United States Patent [19]

Cunningham et al.

[11] 4,398,542
[45] Aug. 16, 1983

[54] PRESSURE DIAPHRAGM

[75] Inventors: Joel N. Cunningham, San Diego; Richard M. Bucchianeri, Escondido; Stephen H. O'Leary, Encinitas, all of Calif.

[73] Assignee: Ivac Corporation, San Diego, Calif.

[21] Appl. No.: 216,650

[22] Filed: Dec. 15, 1980

[51] Int. Cl.³ .............................................. G01L 7/08
[52] U.S. Cl. .................................... 128/675; 73/715; 73/730; 128/748; 604/118; 604/122
[58] Field of Search ........... 128/214 R, 214 E, 214 F, 128/214.2, 673, 274, DIG. 12, DIG. 13, 675, 748; 137/557; 116/270, DIG. 7; 73/715, 730, 146.8; 604/118, 122

[56] References Cited

U.S. PATENT DOCUMENTS

| 69,894 | 10/1867 | Beardslee . | |
|---|---|---|---|
| 1,640,606 | 8/1927 | Joyce . | |
| 2,369,707 | 2/1945 | Baak | 73/395 |
| 2,444,163 | 6/1948 | Kocmich | 200/83 |
| 2,535,998 | 12/1950 | Bierman | 73/389 |
| 2,629,399 | 2/1953 | Kulick | 128/748 X |
| 3,499,434 | 3/1970 | Ullrich et al. | 128/2.05 |
| 3,625,199 | 12/1971 | Summers | 128/748 |
| 3,713,341 | 1/1973 | Madsen et al. | 73/715 |
| 3,818,765 | 6/1974 | Eriksen | 73/395 |
| 3,880,151 | 4/1975 | Nilsson et al. | 128/673 |
| 4,072,056 | 2/1978 | St. Jacques Lee | 73/706 |
| 4,141,252 | 2/1979 | Lodge | 73/730 X |
| 4,227,420 | 10/1980 | Lamadrid | 73/730 X |

FOREIGN PATENT DOCUMENTS 2513490 10/1975 Fed. Rep. of Germany ... 128/214 R

Primary Examiner—Dalton L. Truluck
Attorney, Agent, or Firm—Fulwider, Patton, Rieber, Lee & Utecht

[57] ABSTRACT

A pressure diaphragm, wherein at least a portion of an elongate fluid channel is formed diametrically across, and is open through, a flat raised surface of a substantially rigid, disk-like body, and wherein a flexible membrane overlies the raised surface and is sealed to a surrounding flange. The fluid channel communicates with fluid inlet and outlet fittings carried by the body, which are adapted for connection with the tubes of an IV set, and the cross-sectional flow area of the fluid channel is substantially equal to or less than the cross-sectional flow area of any IV tube adapted for connection to the fluid inlet fitting.

23 Claims, 7 Drawing Figures

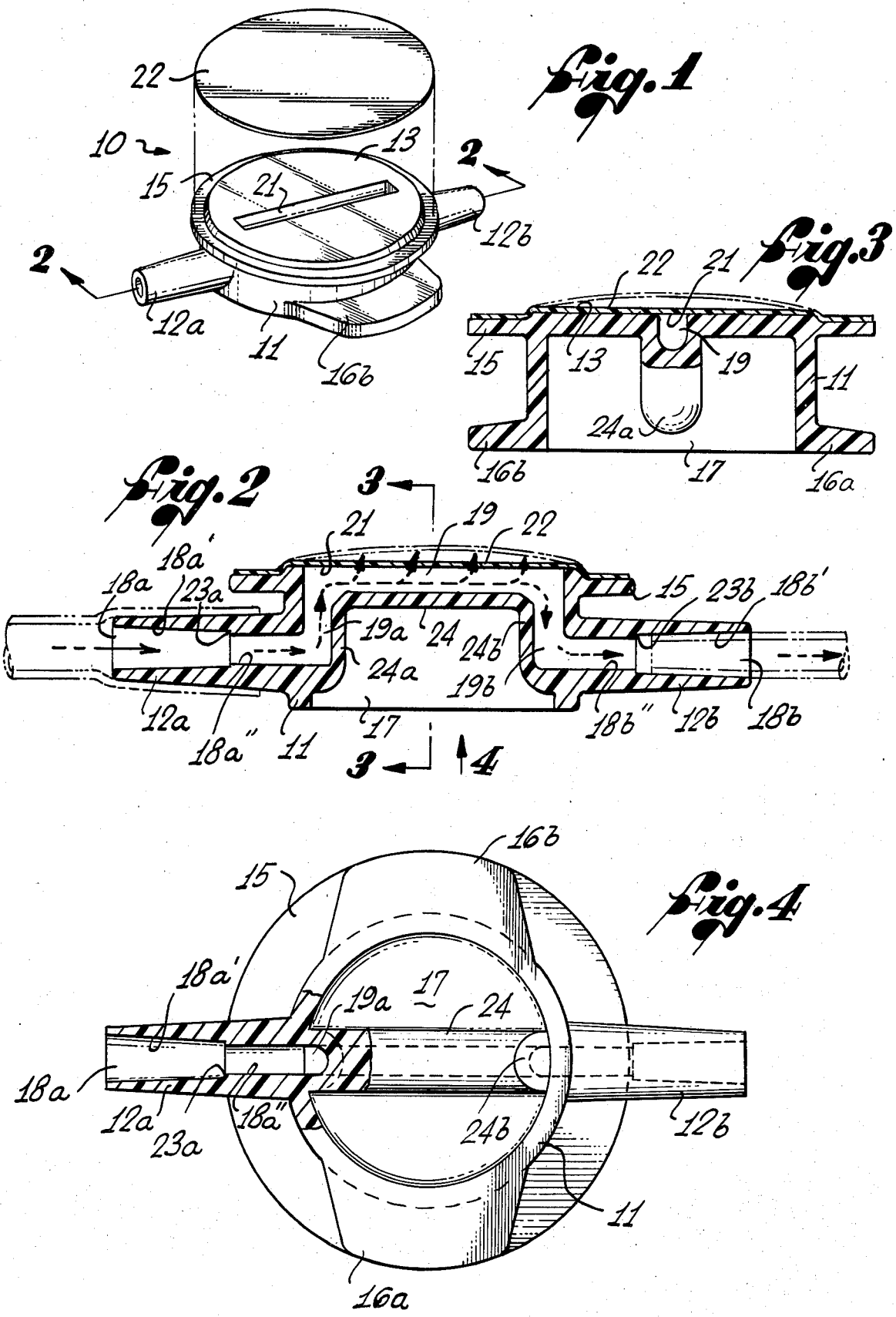

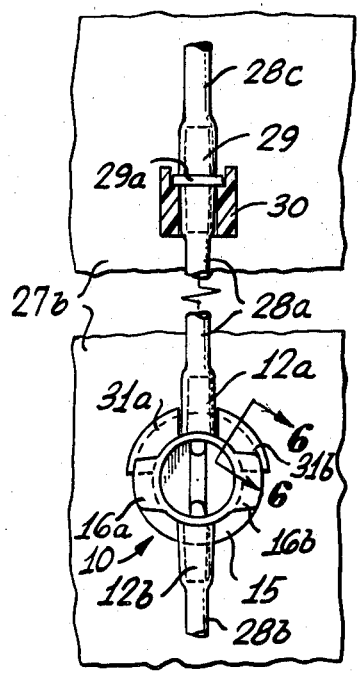
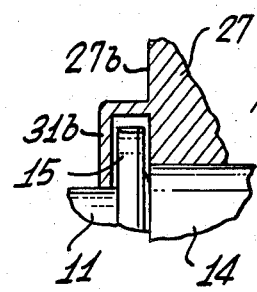
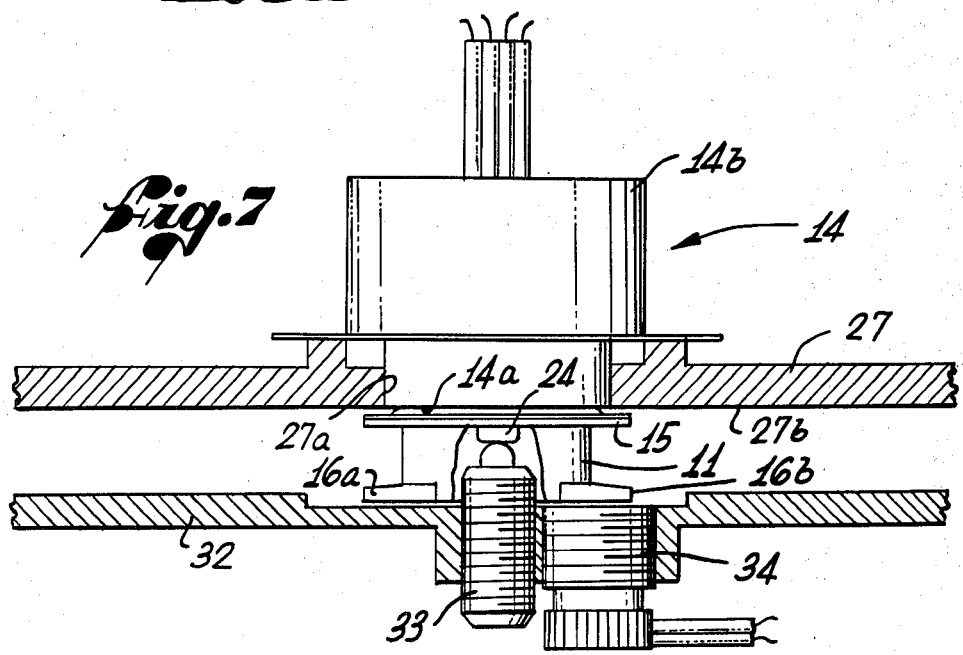

PRESSURE DIAPHRAGM

BACKGROUND OF THE INVENTION

This invention relates generally to fluid pressure measurement, and more particularly, to a new and improved pressure diaphragm by means of which the pressure in a fluid line can be sensed. The invention has particular application in connection with instrument systems for administering parenteral fluids to the human body.

The administration of parenteral fluids to human patients conventionally involves use of a solution administration set. The set typically is a disposable plastic product, and comprises a drip chamber adapted to be connected to a fluid source, a length of tubing extending from the chamber to the patient and a valve mechanism, such as a roller clamp on the tubing.

In recent years, a variety of mechanical and electrical monitoring systems, controllers and infusion pumps have been developed to accomplish the tasks of sensing and regulating the rate of fluid flow into the human body. Such apparatus may include an electromechanical output device for manipulating the tubing of a conventional administration set in a prescribed manner, as by using a series of cam followers that sequentially massage the tubing and generate a peristaltic pumping action. For use in other apparatus, the tubing may include a syringe which is cyclically driven by the electromechanical output device through alternate fill and pump strokes to draw and deliver precise amounts of fluid from the fluid source to the patient. Alternatively, instead of a conventional administration set, a set comprising a length of tubing extending from a self-contained syringe to the patient may be used in an apparatus designed for a single controlled pump stroke to deliver the fluid contained in the syringe to the patient.

A common feature of each of these apparatus is the capability of developing positive pressure in the tubing. Some of the apparatus have also been capable of activating alarms when an out-of-limit condition exists, thus freeing medical personnel to some extent for other duties.

However, while such apparatus have generally served their purpose, there has been a need for an effective, safe and reliable means of sensing fluid pressure in the tubing leading to the patient. Specifically, concerns have been raised about the capability of monitoring and controlling the fluid pressure developed in the tubing by such positive pressure electromechanical devices.

Hence, those concerned with the development and use of fluid administration systems, and particularly those concerned with the design of parenteral administration systems, recognize the need for improvement in devices for sensing fluid pressure.

SUMMARY OF THE INVENTION

Briefly, and in general terms, the present invention resides in a new improved pressure diaphragm, wherein a fluid channel is formed in a rigid body in such a manner as to define a single flow path, the body having an opening through an exterior surface into the channel, with a flexible membrane covering the opening and sealed to the body. The fluid channel is elongate and has a cross-sectional flow area substantially equal to or less than the cross-sectional flow area of any tubing adapted for connection to a fluid inlet fitting carried by the body. In addition, the fluid channel extends through the body as directly as practicable between the fluid inlet fitting and a fluid outlet fitting carried by the body.

More particularly, in a presently preferred embodiment, the opening is formed in a flat, preferably raised exterior surface of the body that is substantially larger than the opening. The membrane is sealed to the body around the periphery of the upper surface, but is not sealed to the upper surface itself. For sealing of the membrane, the body is provided with a flange that surrounds the upper surface.

The presently preferred configuration of the body is that of a relatively thin disk having a pair of gradually tapered, nipple-like fluid fittings projecting radially outwardly from diametrically opposing sides of the body. The fluid channel is defined by a central channel portion directed diametrically across the body, offset towards the upper surface from the fluid fittings, and a pair of connecting channel portions that connect the opposite ends of the central channel portion to the fittings. The central channel portion is entirely open through the upper surface of the body to the membrane.

The pressure diaphragm of the present invention, by reason of the foregoing features, consumes minimal fluid volume, is highly responsive to pressure fluctuations, and is readily purged of air. Thus it is an effective, safe and reliable diaphragm for medical applications.

The above and other advantages of the invention will become apparent from the following more detailed description, when taken in conjunction with the accompanying drawings of a preferred embodiment.

BRIEF DESCRIPTION OF THE DRAWINGS

FIG. 1 is an exploded perspective view of a pressure diaphragm embodying the principles of the invention;

FIG. 2 is an enlarged sectional view taken along the line 2—2 in FIG. 1;

FIG. 3 is a sectional view taken along the line 3—3 in FIG. 2;

FIG. 4 is an enlarged bottom plan view of the pressure diaphragm, partially broken away in section;

FIG. 5 is fragmentary front elevational view, partially in section, and illustrates the pressure diaphragm connected with the tubing of an administration set and held in place against a pressure transducer;

FIG. 6 is a fragmentary sectional view taken along the line 6—6 in FIG. 5; and

FIG. 7 is a horizontal sectional view, partly broken away, showing the pressure diaphragm being held in place between the pressure transducer and a hinged door.

DESCRIPTION OF THE PREFERRED EMBODIMENT

Referring now to the drawings for the purpose of illustrating the presently preferred embodiment of the invention, and particularly to FIG. 1 thereof, there is shown a pressure diaphragm, indicated generally by reference numeral 10, especially adapted for connection with the tubing of an administration set to provide an improved means by which fluid pressure in the tubing can be sensed. In the ensuing description, references will be made to the term "IV", normally referring to intravenous administration, although it is to be understood that this is by way of example only, the present invention having application to other forms of administration.

The pressure diaphragm 10 includes a relatively thin, disk-like body 11 having a pair of gradually tapered nipple-like fittings 12a, 12b projecting radially outwardly from diametrically opposing sides of the body for in-line connection with an IV tube (shown in phantom in FIG. 2). For purposes of description, one fitting will be designated as the fluid inlet fitting 12a, and the other fitting will be designated as the fluid outlet fitting 12b, although it will be apparent that this designation is arbitrary because the diaphragm 10 is symmetrical. Designation of a fluid inlet and a fluid outlet, of course, has reference to the orientation of the diaphragm 10 as connected into the tubing of an IV set.

The body 11 has a flat upper surface 13, which in use will be presented toward an appropriate pressure transducer such as the pressure transducer 14 shown in FIG. 7. The body 11 further includes a relatively thin annular flange 15 that projects radially outwardly from the body near the upper surface. A pair of similarly thin ears 16a, 16b project radially outwardly near the bottom of the body, along a diametric axis normal to the axis defined by the inlet and outlet fittings 12a, 12b. As best shown in FIGS. 2 and 3, the body 11 is generally hollow so as to define a relatively large recess 17 opening out the bottom.

A fluid passageway 18a is formed through the inlet fitting 12a and a like fluid passageway 18b is formed through the outlet fitting 12b. Formed in the body 11 is an elongate fluid channel comprising a central channel portion 19, which is directed diametrically across the body, parallel to the upper surface 13, and a pair of connecting channel portions 19a, 19b directed normal to the upper surface. For convenience, the central channel portion 19 will be referred to hereinafter simply as the central channel 19, while the connecting channel portions 19a, 19b will be referred to simply as the connecting channels 19a, 19b.

The central channel 19 is offset from the inlet and outlet passageways 18a, 18b toward the upper surface 13 and opens through the upper surface to define a slot-like opening 21 therein. The pair of connecting channels 19a, 19b connect the opposite ends of the central channel 19 to the inlet and outlet passageways 18a, 18b, respectively, to complete a fluid path through the diaphragm 10. The central channel 19 and the two connecting channels 19a, 19b are formed by elongate U-shaped channel walls 24, 24a, 24b, respectively, which depend from the interior surface of the body recess 17.

A thin flexible membrane 22 overlies the upper surface 13 and is sealed around the periphery of the upper surface to the annular flange 15. The membrane 22 is not sealed to the upper surface 13 itself. Since the annular flange 15 is formed a step below the upper surface 13, the upper surface and the membrane 22 present a raised area especially adapted for intimate contact with the pressure transducer 14 (FIG. 7). Positive pressure in the fluid being delivered through the IV tube to the patient is transmitted through the opening 21 to the membrane 22, and in turn is applied to the pressure transducer 14.

In phantom lines in FIGS. 2 and 3, the membrane 22 is shown in an expanded state responsive to a positive pressure in the fluid being carried by the IV tubes connected to the fluid inlet and outlet fittings 12a, 12b. In actual use, the extent to which the membrane 22 will expand naturally depends on the opposite reaction force applied to the membrane by a pressure transducer. The pressure transducer 14 shown in FIG. 7 is of the strain gage type and includes a stainless steel diaphragm 14a against which the membrane 22 is held. The voltage in the transducer is proportional to the pressure in the IV tubes. With a pressure transducer of this type, very little deflection of the transducer diaphragm 14a will occur. Other types of transducers or detectors, of course, may be utilized with the pressure diaphragm of the present invention, such as that shown and described in an application, Ser. No. 216,764, filed concurrently herewith, entitled "Pressure Detector," inventor William W. Busche, which is incorporated herein by reference.

Standard medical procedures require that an IV set be primed, i.e., filled with fluid and purged of air, before being connected to a patient. As an aid to priming of the diaphragm 10, it will be appreciated that the fluid path through the diaphragm 10 has been made as direct as practicable by forming the central channel 19 diametrically across the body 11. This in effect creates a single flow path for the fluid and eliminates possible fluid shunting that might result in the trapping of air, particularly under conditions of significant positive fluid pressure, if multiple paths were available for fluid flow.

With regard to having a direct fluid path through the diaphragm 10, however, it will be appreciated that the central channel 19 is offset from the inlet and outlet passageways 18a, 18b so that the inlet and outlet fittings 12a, 12b, and the IV tubes connected thereto, will not protrude above the upper surface 13. Otherwise, it would be more difficult to mount the diaphragm 10 with the membrane 22 intimately pressed against the transducer 14. Consistent with this consideration and the design of the apparatus in which the diaphragm 10 is to be mounted, the precise location and orientation of the fluid fittings 12a, 12b is relatively unimportant, and they could be formed, for instance, projecting directly downward from the connecting channels 19a, 19b, respectively, (i.e. normal to the upper surface 13), rather than radially outwardly from the sides of the body 11.

With further regard to priming of the diaphragm 10, the cross-sectional area of the fluid path through the diaphragm is substantially equal to or less than the internal cross-sectional area of the IV tube connected to the fluid inlet fitting 12a. By making the cross-sectional flow area through the diaphragm 10 substantially equal to or less than the flow area in the IV tube, a single flow path is further insured since the fluid will tend to maintain a unified or "solid" wavefront as it initially flows through the diaphragm during priming, pushing ahead all of the air so that none is left trapped behind.

More specifically, it should be noted that the fluid inlet and outlet fittings 12a, 12b are each adapted for connection to IV tubes of various diameters. In particular, as an optional feature, provision is made for external connection with a relatively large IV tube stretched over the outside of the fittings 12a, 12b, or for internal connection with a relatively smaller IV tube received into the inlet and outlet passageways 18a, 18b.

External connection of a relatively larger IV tube to the fluid inlet fitting 12a is illustrated in phantom in FIG. 2. It will be noted that the outside surfaces of both fittings 12a, 12b taper gradually inwardly towards their free ends, as previously mentioned. The larger IV tube is stretched over the fluid inlet fitting 12a and is held in place by a snug friction fit or solvent weld to the outside surface of the inlet fitting.

To allow internal connection of a relatively smaller IV tube, an outer portion 18a', 18b' of both the inlet and outlet passageways 18a, 18b is tapered gradually inwardly from the free ends of the fittings 12a, 12b, and then the inlet and outlet passageways step to a somewhat smaller, uniform diameter over their remaining inner portions 18a", 18b" that lead to the connecting channels 19a, 19b. The shoulder 23a, 23b thus formed inside each passageway 18a, 18b at the juncture of the outer portions 18a', 18b' and the inner portions 18a", 18b" serves as a limit stop for the smaller tubing. Internal connection of a smaller IV tubing to the outlet fitting 12b is illustrated in phantom in FIG. 2. The portion of the tubing received within the outer portion 18b' of the outlet passageway 18b is slightly compressed and is held in place by means of a solvent weld to the inside surface of the outlet passageway.

From a dimensional standpoint, it will be appreciated that the flow area of the fluid path through the diaphragm 10 is substantially equal to or less than the flow area of the IV tube connected to the inlet fitting 12a, regardless of whether a larger IV tube is externally connected or a smaller IV tube is internally connected to the inlet fitting. By way of example, the relatively larger IV tube referred to above may be a standard tubing having an internal flow area of about 0.0090 sq. in., or it may be a precision-bore elastic tubing having a smaller area of about 0.0048 sq. in. In the presently preferred embodiment of the diaphragm 10, for purposes of comparison, the cross-sectional flow area of both the central channel 19 and two connecting channels 19a, 19b is about 0.0035 sq. in., while the flow area of the inner portion 18a", 18b" of the inlet and outlet passageways 18a, 18b is about 0.0030 sq. in. The flow area of the outer portions 18a', 18b' of each passageway, at the free ends of the fittings 12a, 12b, is about 0.0061 sq. in. A smaller IV tube internally connected to the inlet fitting 12a will have a flow area substantially equal to that of the inner portions 18a", 18b" of the passageways 18a, 18b.

The cross-sectional flow area of the fluid path need not be precisely uniform throughout the body 11 to result in an effective single flow path and, in fact, it will be seen that the flow area increases at the juncture of the central channel 19 with each connecting channel 19a, 19b. Some variation among the flow area of the outer portions 18a', 18b' and the inner portions 18a", 18b" of the inlet and outlet passageways 18a, 18b and the flow area of the connecting channels 19a, 19b is also apparent, for example.

In addition to effective priming, a further advantage of the fluid path design of the diaphragm 10 is that it has a very low internal fluid volume, so that minimal fluid is wasted during priming. Specifically, the fluid path through the diaphragm 10 only consumes about 0.1 ml.

As best shown in FIGS. 2, 3 and 4, both the lateral and longitudinal cross-sectional configurations of the fluid path through the diaphragm 10, moveover, further facilitate effective priming of the diaphragm. In lateral cross-section (FIGS. 3 and 4), the bottom or inside surface of each channel wall 24, 24a, 24b, which together define the fluid path through the body, is rounded to eliminate corners where air bubbles might adhere and also to minimize fluid turbulence. In lateral cross-section (FIG. 2), the respective intersections of the connecting channel walls 24a, 24b with the inner portions 18a", 18b" of the inlet and outlet passageways 18a, 18b also are rounded for the same reasons. Similarly, as shown in FIG. 2, the intersection of the central channel wall 24 with each connecting channel wall 24a, 24b is beveled. The lateral cross-sectional configurations of both the inner portions 18a''', 18b''' and the outer portions 18a', 18b' of the inlet and outlet passageways 18a, 18b are round.

In preparing a conventional IV set for connection to a patient, medical personnel typically prime the IV set not only, of course, before the IV tube is connected to the patient, but also before installing the IV set in a fluid flow control apparatus, such as one of the earlier described instruments capable of developing positive fluid pressure in the IV tube. According to this procedure, priming is accomplished by utilizing gravity-induced fluid flow from the fluid source, which is positioned entirely above the IV set to create a pressure head. In recognition of the fact that the diaphragm 10 may be held or dangled in any orientation while this procedure is carried out, the design of the fluid path is such that, regardless of orientation, all of the air will be purged. Using gravity-induced fluid flow for priming also tends to minimize the possibility of a large initial pressure impulse occurring that could force the membrane 22 away from the upper surface 13 to create a region in which air could be trapped. As an added precaution against this occurring, the membrane 22 can be physically held against the upper surface 13 by the user until priming has been completed.

With some apparatus, priming is intended to be accomplished by first installing the IV set in the fluid control apparatus and utilizing the apparatus to deliver the initial flow of fluid for priming. Alternatively, with the administration set characterized by a self-contained syringe, mentioned earlier, priming can be accomplished by manual operation of the syringe plunger to cause fluid delivery. In either case, the diaphragm 10 can be mounted in place with the membrane 22 held flatly against the upper surface 13 by a pressure transducer, thereby tending to insure that no air becomes trapped between the membrane and the upper surface.

Referring now in detail to FIGS. 5, 6 and 7, one possible arrangement for mounting the pressure diaphragm 10 in place relative to the pressure transducer 14 is illustrated. As best shown in FIG. 7, the pressure transducer 14 includes a housing 14b, mounted by any suitable means to a panel 27, and the aforementioned stainless steel diaphragm 14a that fits flush with the panel face 27b, through an opening 27a in the panel. The transducer diaphragm 14a presents a flat forwardly facing surface against which the membrane 22 of the diaphragm 10 is held.

As shown in FIG. 5, a first IV tube 28a has one end externally connected to the fluid inlet fitting 12a of the diaphragm 10 and has inserted into an opposite end a fitting 29 from which a thin annular flange 29a projects radially outwardly. A second IV tube 28b is externally connected to the fluid outlet fitting 12b and leads to the patient. A third IV tube 28c is connected to the other side of the fitting 29 and extends upwardly to any appropriate fluid source. The first IV tube 28a may be precision-bore elastic tubing especially adapted for manipulation by a series of cam followers (not shown) that generates a peristaltic pumping action.

A slotted bracket 30 having a complimentary recess formed in it to receive the flange 29a is affixed to the panel face 27b above the opening 27a for the pressure transducer diaphragm 14a. A pair of arc-like brackets 31a, 31b, shown in cross-section in FIG. 6, are formed on the panel face 27b centered above the opening 27a and are spaced from each other about a vertical axis to provide clearance for the first IV tube 28.

The diaphragm 10 is mounted by first inserting the fitting 29 into the slotted bracket 30 and then hooking the annular flange 15 of the diaphragm under the arc-like brackets 31a, 31b. This requires a light stretching of the first IV tube 28. A door 32 hinged to the panel 27 (shown only in FIG. 7) is then closed and latched to the panel. A spring plunger 33, which is threaded into the door 32, is received into the recess 17 of the diaphragm body 11 and the leading end of the spring plunger presses against the flat bottom or rear surface of the central channel wall 24. The spring plunger 33 is threaded to allow for calibration adjustment of the force with which the diaphragm 10 is held against the transducer diaphragm 14a.

A photodetector 34 is threaded through an opening in the door 32 immediately to one side of the spring plunger 33 and operates as a means for detecting the presence of the pressure diaphragm 10. The photodetector 34 is a two part device, including both a light emitter and a light sensor, and is so mounted that when the diaphragm 10 is in place, one ear 16b is directly in front of it. Preferably, the ear 16b is white in color and reflects sufficient light back into the photodetector 34 to indicate the presence of the diaphragm 10. If the diaphragm 10 is not in place, much less, if any, light is reflected and the photodetector 34 is effective to sense that the diaphragm is absent. The output of the photodetector is utilized by the fluid flow control apparatus to trigger appropriate alarms or otherwise signal the absence of the diaphragm 10 to the user.

For ease of manufacture and structural integrity, the body 11 and the inlet and outlet fittings 12a, 12b are molded as an integral unit of a biologically compatible material, such as rigid PVC. It will also be appreciated that the geometry of the body 11, and in particular the configuration of the fluid path through the diaphragm 10, and the opening 21, have been selected to avoid undercuts, which otherwise would make manufacture of the body as an integral unit more difficult and expensive.

With reference to the remaining dimensions of the diaphragm 10, the overall length of the diaphragm, including the inlet and outlet fittings 12a, 12b, is about one-and-five-eighths inches and the overall thickness of the diaphragm is about three-tenths of an inch. The inlet and outlet fittings 12a, 12b are about one-half inch in length and both the annular flange 15 and the ears 16a, 16b project outwardly about one-eighth inch.

The membrane 22 is about eight-thousandths of an inch thick and comprises a flexible, biologically compatible material, such as a PVC film. Preferably the membrane 22 has a fine taffeta finish on the outside to help insure that it does not adhere to the transducer diaphragm 14a, particularly since it has a polished stainless steel finish. Any suitable means can be used to seal the periphery of the membrane 22 to the annular flange 15, such as by dialectric sealing.

The new and improved pressure diaphragm of the present invention is extremely convenient, safe and reliable to use, and inexpensive to manufacture. The diaphragm provides a rapid response to changes in pressure and is designed to insure, with proper usage, that no air will become trapped therein, either during priming or normal use, regardless of the orientation of the diaphragm.

It will be apparent from the foregoing that, while a particular form of the invention has been illustrated and described, various modifications can be made without departing from the spirit and scope of the invention. Accordingly, it is not intended that the invention be limited except as by the appended claims.

We claim:
1. A pressure diaphragm comprising:
a substantially rigid body;
fluid inlet means carried by said body for connection to a first IV tube;
fluid outlet means carried by said body for connection to a second IV tube;
a continuously elongated fluid channel formed in said body, one end of said fluid channel communicating with said fluid inlet means and the opposite end of said fluid channel communicating with said fluid outlet means, said fluid channel having a substantially uniform cross-sectional flow area that is substantially equal to or less than the cross-sectional flow area of said first IV tube, and at least a portion of said channel defining an opening through an exterior surface of said body; and
a flexible membrane overlying said opening and sealed to said body around said opening, whereby fluid pressure in said first and second IV tubes is transmitted through said opening to said membrane.

2. A pressure diaphragm as set forth in claim 1, wherein said fluid channel extends substantially directly between said fluid inlet means and said fluid outlet means.

3. A pressure diaphragm as set forth in claim 1, wherein said exterior surface is flat.

4. A pressure diaphragm as set forth in claim 1, wherein said exterior surface is substantially larger than said opening.

5. A pressure diaphragm as set forth in claim 4, wherein said membrane is sealed to said body around the periphery of said exterior surface.

6. A pressure diaphragm as set forth in claim 5, wherein said exterior surface is a raised surface.

7. A pressure diaphragm comprising:
a substantially rigid body;
fluid inlet means, carried by said body, for connection to a first IV tube;
fluid outlet means, carried by said body, for connection to a second IV tube;
a fluid channel formed in said body, at least a portion of said channel defining an opening through an exterior surface of said body, said channel communicating with both said fluid inlet means and said fluid outlet means, and said channel further having a cross-sectional flow area substantially equal to or less than the cross-sectional flow area of said first IV tube; and
a flexible membrane overlying said opening and sealed to said body around said opening, whereby fluid pressure in said first and second IV tubes is transmitted through said opening to said membrane.

8. A pressure diaphragm as set forth in claim 7, wherein said fluid channel extends substantially directly between said fluid inlet means and said fluid outlet means.

9. A pressure diaphragm as set forth in claim 8, wherein said fluid channel is elongate.

10. A pressure diaphragm as set forth in claim 7, wherein said exterior surface is flat.

11. A pressure diaphragm as set forth in claim 10, wherein said exterior surface is substantially larger than said opening.

12. A pressure diaphragm as set forth in claim 11, wherein said membrane is sealed to said body around the periphery of said exterior surface.

13. A pressure diaphragm as set forth in claim 10, wherein said exterior surface is a raised surface.

14. A pressure diaphragm as set forth in claim 9, wherein said fluid inlet coupling means and said fluid outlet coupling means are formed with said body as an integral unit.

15. A pressure diaphragm comprising:
a relatively thin, disk-like body having an upper surface;
a fluid inlet fitting carried by said body and adapted for connection to a first IV tube;
a fluid outlet fitting carried by said body and adapted for connection to a second IV tube;
a continuously elongated fluid channel formed in said body, said fluid channel having a substantially uniform cross-sectional flow area that is substantially equal to or less than the cross-sectional flow area of said first IV tube, said fluid channel including a central channel portion directed diametrically across said body, said central channel portion opening through said upper surface, and said fluid channel further including a first connecting channel portion connecting one end of said central channel portion to said fluid inlet fitting and a second connecting channel portion connecting the other end of said central channel portion to said fluid outlet fitting; and
a thin flexible membrane overlying said upper surface and sealed to said body only around the periphery of said upper surface, whereby fluid pressure in said first and second IV tubes is transmitted through said opening to said membrane.

16. A pressure diaphragm as set forth in claim 15, wherein said body further includes an annular flange projecting radially outwardly from said body adjacent said upper surface, said membrane being sealed to said flange.

17. A pressure diaphragm as set forth in claim 16, wherein said upper surface is raised above said flange.

18. A pressure diaphragm as set forth in claim 17, wherein said upper surface is substantially larger than said opening.

19. A pressure diaphragm as set forth in claim 15, wherein said fluid inlet fitting and said fluid outlet fitting are disposed on diametrically opposite sides of said body.

20. A pressure diaphragm as set forth in claim 19, wherein said fluid inlet fitting and said fluid outlet fitting are nipples that project radially outwardly from said body.

21. A pressure diaphragm comprising:
a relatively thin, disk-like body having a flat upper surface;
a fluid inlet fitting carried by said body and adapted for connection to a first IV tube;
a fluid outlet fitting carried by said body and adapted for connection to a second IV tube;
an elongated fluid channel formed in said body, said fluid channel having a cross-sectional flow area substantially equal to or less than the cross-sectional flow area of said first IV tube, said fluid channel including a central channel portion directed diametrically across said body and opening through said upper surface, and said fluid channel further including a first connecting channel portion connecting one end of said central channel portion to said fluid inlet fitting and a second connecting channel portion connecting the other end of said central channel portion to said fluid outlet fitting; and
a thin flexible membrane overlying said upper surface and sealed to said body only around the periphery of said upper surface, whereby fluid pressure in said first and second IV tubes is transmitted through said membrane.

22. A pressure diaphragm as set forth in claim 21, wherein said upper surface is substantially larger than said opening.

23. A pressure diaphragm as set forth in claim 22, wherein said body further includes an annular flange projecting radially outwardly from said body adjacent said upper surface, said membrane being sealed to said flange, and further wherein said upper surface is raised above said flange.

* * * * *